US006977986B1

(12) United States Patent
Beanland et al.

(10) Patent No.: US 6,977,986 B1
(45) Date of Patent: Dec. 20, 2005

(54) METHOD AND APPARATUS FOR ALIGNING A CRYSTALLINE SUBSTRATE

(75) Inventors: Richard Beanland, Northampton (GB); Derrick Gordon Hart, Northampton (GB)

(73) Assignee: Bookham Technology PLC, Abingdon (GB)

( * ) Notice: Subject to any disclaimer, the term of this patent is extended or adjusted under 35 U.S.C. 154(b) by 0 days.

(21) Appl. No.: 10/148,318

(22) PCT Filed: Nov. 7, 2000

(86) PCT No.: PCT/GB00/04265

§ 371 (c)(1),
(2), (4) Date: Aug. 15, 2002

(87) PCT Pub. No.: WO01/40876

PCT Pub. Date: Jun. 7, 2001

(30) Foreign Application Priority Data

Nov. 29, 1999 (GB) .................... 9928076

(51) Int. Cl.[7] .............................................. G21K 5/00
(52) U.S. Cl. ......................................... 378/34; 378/71
(58) Field of Search .................................... 378/34, 71

(56) References Cited

U.S. PATENT DOCUMENTS

| 4,187,431 A | 2/1980 | Hundt ......................... 250/492 |
| 4,470,875 A | 9/1984 | Poteat ......................... 156/644 |
| 4,668,089 A | 5/1987 | Oshida et al. ............... 356/152 |
| 5,073,918 A * | 12/1991 | Kamon ......................... 378/205 |
| 5,118,953 A | 6/1992 | Ota et al. .................... 250/548 |
| 5,559,601 A | 9/1996 | Gallatin et al. .............. 356/363 |
| 5,600,698 A | 2/1997 | Terashima et al. ............ 378/34 |
| 5,859,439 A | 1/1999 | Nam et al. ................... 250/548 |

FOREIGN PATENT DOCUMENTS

| JP | 63078016 A | 4/1988 |
| JP | 63155722 A | 6/1988 |
| JP | 63307727 A | 12/1988 |

* cited by examiner

*Primary Examiner*—Craig E. Church
(74) *Attorney, Agent, or Firm*—Fleshner & Kim LLP

(57) ABSTRACT

The invention provides an apparatus (10, 300) incorporating a lithographic tool (20) for printing a pattern from a mask (35) onto a substrate, for example a wafer (190), together with a substrate angle measuring tool (100, 310) employing X-ray diffraction techniques for determining substrate crystallographic orientation. The apparatus (10, 310) is calibrated so that the mask (35) is correctly angularly orientated with respect to the measuring tool (100, 310). When a new substrate (190) is loaded into the apparatus (10, 310) for having the pattern from the mask (35) printed thereonto, the apparatus (10, 300) angularly aligns the substrate (190) relative to the measuring tool (100, 310), thereby also aligning it angularly to the mask (35). The apparatus (10, 300) does not utilise any flats on the substrate for angular alignment purposes; as a consequence, the apparatus (10, 300) is capable of providing a high degree of accuracy when aligning crystal planes of the substrate (190) to features on the mask (35), the degree of accuracy approaching one minute of arc or better.

23 Claims, 3 Drawing Sheets

METHOD AND APPARATUS FOR ALIGNING A CRYSTALLINE SUBSTRATE

This application claims priority to PCT/GB00/04265, filed Nov. 7, 2000, published on Jun. 7, 2001, Publication No. WO 01/40876 A1 in the English language and which claimed priority to GB Patent Application No. 9928076.0, filed Nov. 29, 1999.

The present invention relates to a method of aligning a crystalline substrate, for example a semiconductor wafer, so that one or more of its crystal planes are aligned to lithographic patterns to be transferred onto the substrate by lithographic processes; moreover, the invention also relates to an apparatus for performing the method.

In conventional microfabrication of semiconductor devices, a semiconductor wafer is subjected to lithographic processes for delineating features thereon, the wafer being chemically processed in conjunction with the lithographic processes to transform the features into functional parts of the devices; when the lithographic and chemical processes are completed, the wafer is finally cleaved to separate out the individual devices for subsequent packaging and testing prior to being delivered to customers.

Such devices are often manufactured such that the lithographic patterns are aligned to crystallographic plane directions of the wafer, the wafer being of single crystal structure. For example, optoelectronic devices microfabricated from III–V semiconductor wafers conventionally rely on the generation during their manufacture of smoothly cleaved {110} crystal plane facets therein which play an essential role in device operation, for example providing mirror surfaces for solid-state laser cavities. Generation of such smoothly cleaved facets can be difficult to achieve and requires that the lithographic patterns used to manufacture the devices are very accurately aligned parallel to required cleavage planes of the wafers. This problem is further complicated in that wafers are often deliberately cut during their manufacture so that their major surface planes are not precisely parallel but different by a cutoff angle to the {001} plane of single crystal material comprising the wafers. The cutoff angle can be in a range of 2° to 10° for example. Such wafers are now in routine use in semiconductor processing plants, the non-zero cutoff angle aiding epitaxial growth of crystal layers during fabrication of devices, such layers forming part of the devices.

Conventionally, circular single-crystal silicon wafers and smaller 75 mm diameter single-crystal III–V compound wafers are supplied to semiconductor device manufacturers with ground and polished "flats" at peripheral edges of the wafers, the flats nominally aligned to a particular wafer crystal plane. Larger III–V compound wafers having a diameter of 150 mm or greater do not usually incorporate flats at their peripheral edges but notches instead, the notches typically providing an angular alignment accuracy to wafer crystal planes to an error limit of +/−1°. In the case of smaller III–V material wafers, flats on the wafers are nominally aligned to their {110} crystal plane. Lithographic tools currently operate by mechanically registering to these flats thereby angularly aligning lithographic patterns on lithographic masks within the tools to the flats and hence to crystal planes associated with the flats. However, the angular alignment accuracy of these flats is often insufficient to give accurate alignment for wafer cleaving purposes to provide smoothly cleaved device surfaces. Such inaccuracy is particularly problematic in wafers with non-zero cutoff angle or where epitaxial layers grown during device fabrication also grow onto the flats thereby adversely affecting their registration accuracy.

When fabricating optoelectronic devices, the intersection of a required cleavage plane of a wafer to a major surface plane of the wafer will often need to be parallel to a lithographic pattern for projection onto the wafer to an angular error of less a minute of arc. For example, cleavage tracks between devices in a wafer will in some circumstances be limited to a width of 100 μm in order to ensure sufficient device density on the wafer; if the wafer is of 75 mm diameter, the wafer must be aligned to within +/−2.25 minutes of arc otherwise, when devices are cleaved along crystal planes of the wafer, the cleavage will propagate laterally beyond the cleavage track thereby adversely affecting device yield. This problem of alignment accuracy is further exacerbated when larger diameter wafers are used, for example 150 mm diameter wafers. To alleviate this alignment problem, it is convention practice to employ cleavage tracks wider than 100 μm and accept an associated reduction in device density on wafers.

There are currently two known solutions to the problem of aligning lithographic patterns to wafer crystal planes by mechanical registration to associated wafer flats. In a first solution, a wafer is cleaved along a required plane spatially close to an existing nominally accurate flat on the wafer; a cleaved surface thereby generated is accurately angularly aligned to wafer crystal planes and can be used for mask pattern alignment purposes. In a second solution, a wafer is supplied by its manufacturer with a flat on the wafer, the flat being unpolished so that its accuracy is not degraded by polishing operations.

Both of the two solutions provide sufficiently accurately aligned flats to which lithographic tools can register to within an error of a few minutes of arc. However, such cleaved and unpolished flats are known to be a source of cracks which can propagate across wafers comprising such flats, thereby resulting in failure of devices manufactured from the wafers or even breakage of the wafers. Wafer flats are conventionally polished and rounded in order to reduce risks of associated device failure and wafer breakage. Thus, use of wafers with cleaved or unpolished registration flats represents a serious risk in device manufacturing yield and is preferably avoided.

The inventors have appreciated that the use of conventional flats and notches for performing wafer crystallographic alignment to lithographic patterns is an unsatisfactory approach and therefore represent a problem. In order to address this problem, the inventors have appreciated that alternative alignment techniques can be employed.

According to a first aspect of the present invention, there is provided a method of aligning a substrate in an apparatus, characterised in that the apparatus incorporates a lithographic tool for printing a pattern onto the substrate and a diffractive substrate angle measuring tool for measuring angular orientation of one or more crystal planes of the substrate, the method including the steps of:

(a) calibrating angular orientation of the pattern relative to the measuring tool;
(b) inserting the substrate into the lithographic tool; and
(c) measuring angular orientation of said one or more crystal planes of the substrate using the measuring tool, and rotating the substrate until its one or more crystal planes angularly align to the pattern;

the pattern thereby angularly aligned to the substrate and to said one or more crystal planes thereof.

The invention provides the advantage that the apparatus is capable of aligning crystal planes of the substrate to the pattern without relying on any flats or similar alignment features incorporated into the substrate.

Advantageously, the diffractive measuring tool used in the method operates at X-ray radiation wavelengths to determine angular orientation of said one or more crystal planes.

Use of X-ray radiation provides the advantage that its wavelength is in the same order of magnitude as distances between atoms forming the substrate, thereby providing diffracted X-ray beams at conveniently measurable angles relative to the substrate. The measuring tool preferably measures diffracted X-ray radiation resulting from Bragg diffraction within the substrate.

In order to make the method simple and reliable, it is desirable that correct angular orientation of said one or more crystal planes is determined by finding an orientation of the substrate relative to the measuring tool resulting in a maximum X-ray count rate in an X-ray detector of said measuring tool. Such an approach circumvents a need to perform complex calculations associated with alternative crystal orientation measurement techniques which involve complex computing and extrapolation of diffracted beams.

Conveniently, in the method, a diffracted X-ray beam is generated for measuring angular orientation of said one or more crystal planes by transmitting an interrogating X-ray beam through the substrate.

However, transmission of X-ray radiation through the substrate results in attenuation of the radiation. Thus, advantageously in the method, a diffracted X-ray beam is generated for measuring angular orientation of said one or more crystal planes by reflecting an interrogating X-ray beam from the substrate. There arises thereby the benefit that a relatively higher proportion of X-ray radiation incident on the substrate is diffractively reflected compared to a proportion transmitted and diffracted through the substrate. Preferably, so as not to obscure the lithographic tool, the interrogating beam impinges onto a peripheral edge of the substrate.

Moreover, in the method, it is desirable to keep the measuring tool to one side of the lithographic tool so as not to obstruct the lithographic tool. Thus, advantageously in the method, the measuring tool uses first, second or third order diffraction modes to measure angular orientation of said one or more crystal planes. Diffraction modes higher than first order result in relatively greater diffraction angles thereby enabling the measuring tool to be mounted well towards one side of the lithographic tool.

In the aforementioned method, calibration is preferably achieved using a sub-method, the sub-method including the steps of:

(a) inserting a test substrate into the lithographic tool, the test substrate being cleaved to expose a cleaved edge corresponding to a crystal plane;
(b) angularly aligning the test substrate relative to the measuring tool to yield a maximum radiation count rate from its detector; and
(c) angularly aligning features of the pattern relative to the cleaved edge.

Use of a cleaved test wafer ensures that the pattern is aligned to the cleaved edge which corresponds to a particular crystal plane.

According to a second aspect of the invention, there is provided an apparatus for performing the method according to the first aspect of the invention, the apparatus comprising a lithographic tool for printing a pattern onto a substrate and a diffractive substrate angle measuring tool for measuring angular orientation of one or more crystal planes of the substrate, the apparatus operable to angularly align said one or more crystal planes to the pattern and then print the pattern onto the substrate.

The apparatus provides the advantage that it is capable of aligning the substrate to the pattern without making reference to any alignment flat present on the wafer.

Advantageously, the measuring tool includes an X-ray source and an X-ray detector, the source arranged to generate a beam for interrogating the substrate and the detector arranged to receive diffracted radiation resulting from Bragg diffraction of the beam. X-ray Bragg diffraction is a convenient accurate approach to measuring crystallographic orientation of the substrate.

Beneficially, the measuring tool is disposed to detect radiation transmitted and diffracted through the substrate. Alternatively, the measuring tool is disposed to detect radiation reflected and diffracted from the substrate. A greater proportion of radiation is reflected from the substrate compared to that transmitted therethrough, thus use of reflected diffracted X-ray radiation provides a relatively greater signal for use in determining substrate crystal orientation and thereby potentially greater accuracy. When reflected radiation is used to determine substrate orientation, it is desirable that a large area X-ray detector for detecting diffracted radiation reflected from the substrate; large in this context means a detector having an X-ray sensitive detecting area in excess of 1 $cm^2$.

The X-ray source preferably includes an X-ray target for generating radiation for the beam, the target being of a material including copper, cobalt, iron or molydenum. Such targets provide useful ranges of X-ray radiation wavelengths for use in the apparatus.

Conveniently, the measuring tool is disposed in two parts adjustably mounted with respect to the lithographic tool, thereby enabling adjustment of the measuring tool to cater for a range of Bragg diffraction angles associated with radiation diffracted from the substrate.

Such a configuration for the measuring tool enables it to be adapted for measuring crystallographic orientations for different compositions and sizes of substrate. Moreover, in order to enable a convenient set-up angle to be adopted for the measuring tool, the measuring tool is operable to function in first second or third order diffraction modes as appropriate.

Embodiments of the invention will now be described, by way of example only, with reference to the following diagrams in which.

Figure 1:
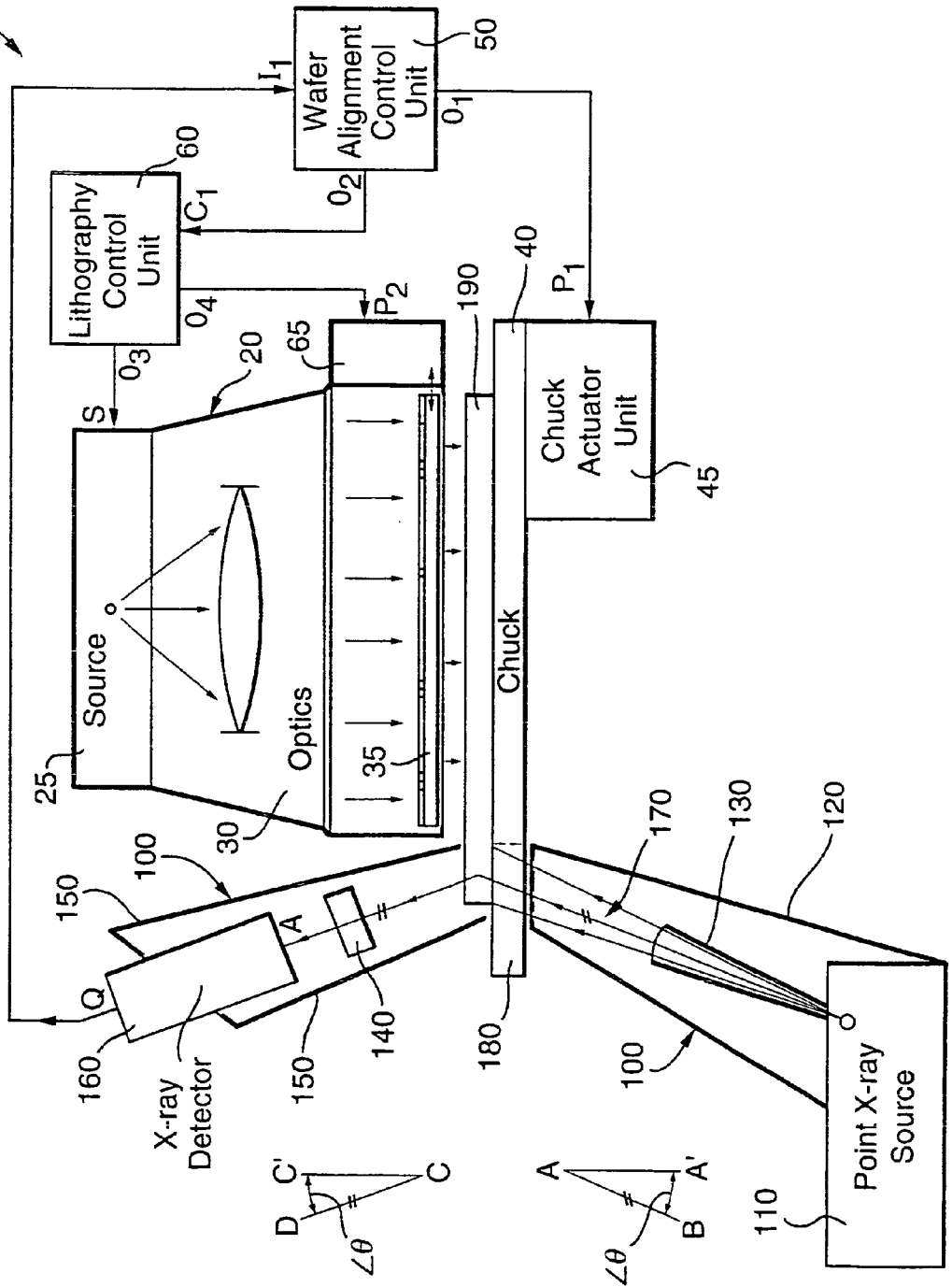
FIG. 1 is an illustration in side view of a first embodiment of an apparatus according to the invention employing X-ray transmissive diffraction.

Referring now to FIG. 1, there is shown an apparatus according to the invention indicated by 10. The apparatus 10 comprises a conventional lithographic tool indicated by 20, the tool 20 including a source of radiation 25 for exposing organic wafer resist, an optical unit 30 for collimating radiation from the source 25, and a lithographic mask 35 comprising a lithographic pattern. The lithographic tool 20 further comprises a wafer chuck 40 linked to an associated actuator unit 45 whose input $P_1$ is connected to an output $O_1$ of a wafer alignment control unit 50. The control unit 50 incorporates a computer for controlling angular rotation of the chuck 40 in response to count signals received at its input $I_1$; the control unit 50 is also arranged to receive input instructions from human operators, for example when the apparatus 10 is operated manually. The control unit 50 is further connected at its output $O_2$ to an input $C_1$ of a lithography control unit 60. The control unit 60 is connected at its output $O_3$ to an input S of the source 25 for controlling when the source 25 emits radiation to irradiate the mask 35. Moreover, the control unit 60 further comprises an output $O_4$ connected to an input $P_2$ of a mask actuator unit 65 for controlling angular rotation of the mask 35.

The apparatus 10 additionally includes an X-ray diffraction tool indicated by 100; a first part of the tool 100 is located beneath and to one side of the chuck 40, and a second part of the tool is located above and to one side of the chuck 40 as illustrated in FIG. 1. The first part of the tool 100 comprises a point X-ray source 110, a first X-ray shield 120 and an X-ray collimator 130. The shield 120 is included to shield the chuck 40 and human operators of the apparatus 10 from stray X-ray radiation which has not been formed into a beam by the collimator 130 and which is scattered at the chuck 40. The source 110 is a 35 kV water-cooled commercial X-ray source including a copper target and operable to emit predominantly X-ray radiation at a wavelength of 0.154 nm although components at other wavelengths away from 0.154 nm are also emitted The collimator 130 comprises a metallic tube, for example a brass tube, which transforms X-ray radiation emitted from the source 110 into a beam of rays of maximum semi-angle greater than the cutoff angle of any wafer to be loaded onto the chuck 40 and angularly aligned. The collimator 130 is enclosed within the first shield 120 which extends from the source 110 to just beneath the chuck 40.

The second part of the tool 100 comprises a beam direction discriminator 140, a second X-ray shield 150 and an X-ray detector 160. The discriminator 140 and a part of the detector 160 sensitive to X-ray radiation are enclosed within the second shield 150 which extends from the detector 160 to just above the chuck 40. The discriminator 140 is implemented using a four-bounce channel cut crystal which exhibits a relatively high transmission factor and a high sensitivity to beam direction, the discriminator 140 also functioning as a monochromator to remove unwanted X-ray components away from 0.154 nm wavelength emitted by the source 110.

The discriminator 140 can alternately be implemented as a pair of slits, one slit of the pair being positionally adjustable relative to the other slit of the pair. However, this implementation of the discriminator 140 requires a monochromator to be included elsewhere between the source 110 and the detector 160.

The source 110 is operable to generate X-ray radiation at a wavelength of 0.154 nm which propagates through the collimator 130 and is partially collimated therein to provide a beam of rays indicated by 170. The beam 170 propagates through a slot 180 in the chuck 40 and also through an edge region of a semiconductor wafer 190 on the chuck 40 whereat the beam 170 is Bragg diffracted and propagates further therefrom through the discriminator 140 to the detector 160 whereat the beam 170 is detected to generate an output signal at an output Q of the detector 160. The output Q is connected to an input $I_1$ of the control unit 50. The control unit 50 is operable to use the output signal from the detector 160 as feedback for controlling the angular alignment of the wafer 190 relative to the diffraction tool 100.

In the apparatus 10, the diffraction tool 100 is aligned relative to the chuck 40 to collect X-ray radiation diffracted from a preferred crystal plane of the wafer 190 on the chuck 40. Moreover, the lithographic tool 20 can include an optical proximity printer, and step-and-repeat optical printer system, or an electron-beam lithographic system. When the tool 20 is an electron-beam system, the wafer 190 and the chuck 40 are located within a vacuum chamber of the system.

The X-ray shields 120, 150 are included in the diffraction tool 100 to reduce stray X-ray radiation therefrom exposing organic resist coating an upper major surface of the wafer 190 facing towards the source 25. Moreover, the shields 120, 150 also protect human operators of the apparatus 10 from harmful X-ray exposure.

Operation of the apparatus 10 will now be described with reference to FIG. 1.

Initially, the mask 35 is rotated to calibrate its angular alignment relative to the diffraction tool 100 to a high degree of accuracy, for example to an error considerably less than 1 minute of arc. Such calibration is achieved by inserting a test wafer onto the chuck 40, the wafer including therein a relatively long cleaved edge which is aligned to its crystal planes to a required degree of angular accuracy for the apparatus 10. X-ray radiation from the source 110 propagates through the collimator 130 to form the beam 170 which further propagates through the slot 180 to the test wafer whereat it is diffracted to generate a diffracted beam. The diffracted beam passes through the discriminator 140 and is eventually detected at the detector 160 to generate a signal at the output Q, the signal taking the form of a series of pulses corresponding to detected X-ray photons. The control unit 50 monitors the rate at which the pulses are provided at the output Q of the detector 160 and instructs the actuator unit 45 to rotate the chuck 40 until the X-ray pulse rate from the detector 160 reaches a maximum. By human visual inspection, for example by using a split screen microscope, instructions are input to the control unit 60 to precisely rotate the mask 35 until projected features thereon precisely angularly align with the cleaved edge on the test wafer. When this alignment is achieved, the mask 35 has thereby been aligned through the test wafer to the diffraction apparatus 100. Calibration is required each time the mask 35 is changed or periodically to correct for drift in the apparatus 10.

During normal operation of the apparatus 10 when it is not being calibrated, the wafer 190 is loaded onto the chuck 40. The control unit 50 monitors the X-ray pulse rate from the detector 160 and instructs the actuator unit 45 to rotate the wafer 190 on the chuck 40 until the X-ray pulse rate is maximised. A maximum X-ray pulse rate occurs when crystal planes within the wafer 190 are aligned to an acceptance angle of the discriminator 140 and hence to the diffraction apparatus 100. The alignment control unit 50 then outputs a signal at its output $O_2$ to the lithography control unit 60. The control unit 60 then registers the mask 35 relative to the wafer 190. When registration of the wafer 190 has been achieved, the control unit 60 then activates the source 25 to illuminate the mask 35, thereby transferring mask features onto a layer of organic resist coated onto the wafer 190 on its major surface facing towards the mask 35.

After exposure, the wafer 190 is removed from the chuck 40, the resist layer is then developed in an appropriate solvent and the wafer 190 subjected to chemical-processing, for example reactive ion etching or ion milling, the resist layer providing a stencil for the processing.

The apparatus 10 provides the benefit in comparison to conventional lithographic tools that it circumvents a need for a precisely orientated flat on the wafer 190 for wafer angular alignment purposes. The apparatus 10 has the potential of providing an alignment accuracy of mask features to wafer crystal orientation limited to the accuracy of calibration of the apparatus 10. Moreover, operation of the apparatus 10 does not demand that its control unit 50 perform complex mathematical data processing thereby enabling angular alignment of a wafer mounted on the chuck 40 to be achieved in the order of seconds.

The source 110 functions as a point source to cater for variations in the cutoff angle of the wafer 190. The semi-angle of the beam of rays 170 is such that at least some rays directed towards the wafer 190 are at an angle which can be Bragg diffracted to propagate through the discriminator 140 into the detector 160.

In FIG. 1, axes A–A' and C–C' are normal to a major surface plane of the wafer 190. Optical axes of the first and second parts of the diffraction apparatus 100 are parallel to the axes B-A and C-D respectively. There is subtended an angle $\alpha$ between the axes A–A' and A-B. Likewise, there is subtended an angle $\theta$ between the axes C–C' and C-D. This angle in FIG. 1 is in the order of 20° to 25° for first order <220> diffraction for 0.154 nm wavelength X-ray radiation when the wafer 190 comprises gallium arsenide; the Bragg diffraction angle depends upon the spacing and relative spatial grouping of atoms in the wafer 190 hence the apparatus 10 is designed so that the angle $\theta$ can be varied to cater for different wafer compositions, for example silicon, indium phosphide as well as gallium arsenide.

In some situations, it is inconvenient to have the diffraction apparatus 100 located closely to the lithography tool 20. This close location can result, from practical considerations, in a relatively long radiation path length from the source 110 to the detector 160. It is feasible to use second <440>, or even third order <660>, diffraction from the wafer 190 enabling the angle $\theta$ to be increased to 50° and greater, thereby conveniently moving most of the diffraction tool 100 off to one side of lithography tool 20; such an arrangement for the diffraction tool 100 enables the path length from the source 110 to the detector 160 to be reduced resulting in the apparatus 10 being more compact.

Moreover, different wavelengths of X-ray radiation other than 0.154 nm can be used in the diffraction tool 100 to achieve a desired angle $\theta$. Different radiation wavelengths can be achieved by replacing the copper target in the source 110 with corresponding targets of silver, iron, molybdenum or even cobalt for example. Preferably, the source 110 is air-cooled rather than water cooled thereby resulting in a more compact unit.

The apparatus 10 suffers a drawback that considerable attenuation of X-ray radiation through the wafer 190 occurs, such attenuation being determined by comparing the amount of X-ray radiation received by the wafer 190 with the amount of radiation received at the discriminator 140 from the wafer 190. There arises a further drawback in that a 2–5 mm peripheral region of the wafer 190 becomes exposed to X-ray radiation thereby diminishing useable wafer 190 area in which devices can be fabricated. Moreover, as will now be described with reference to FIGS. 2 and 3, reflective diffraction provides a improved accuracy compared to transmissive diffraction employed in the aforementioned apparatus 10.

Figure 2:
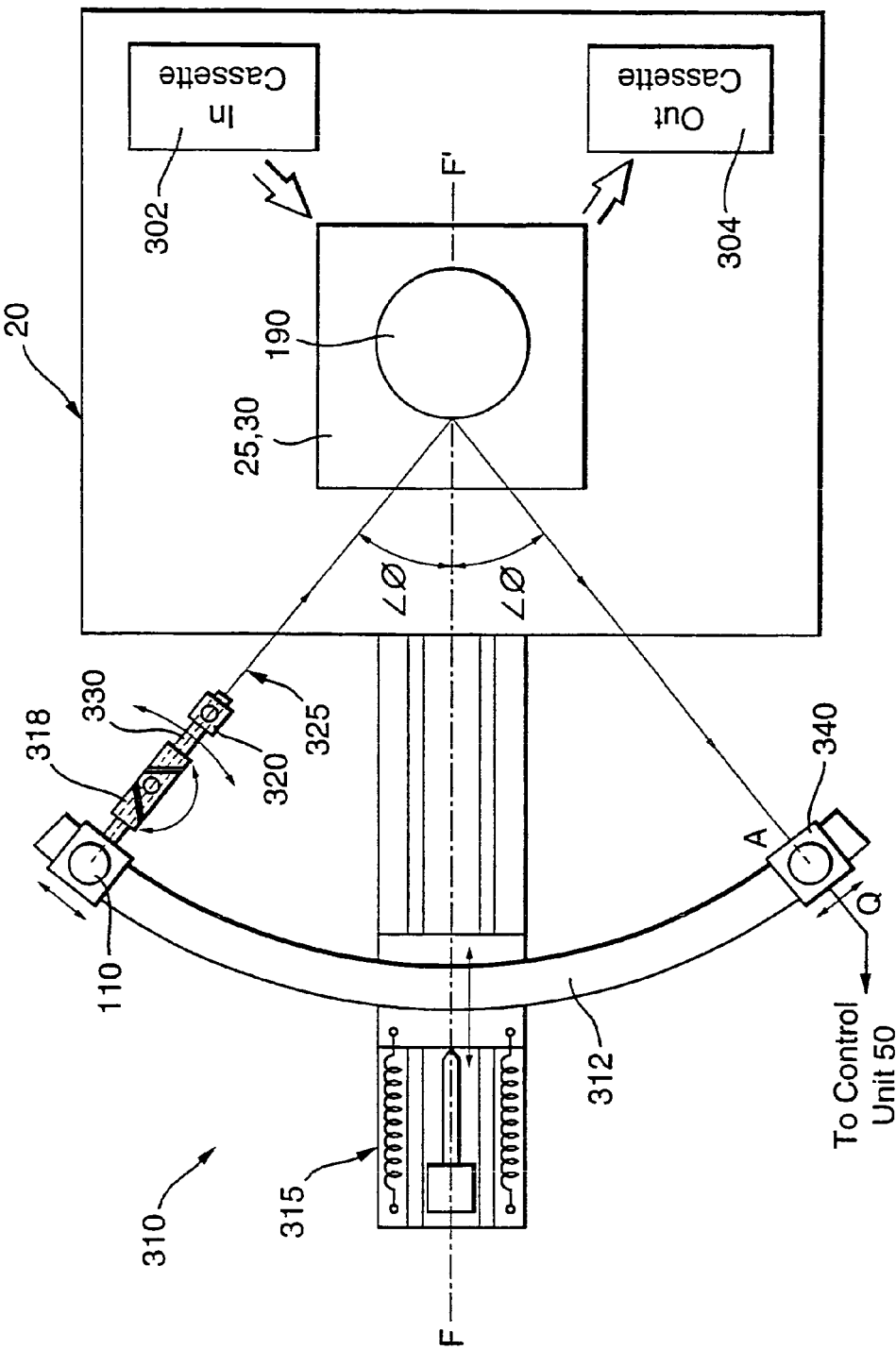
FIG. 2 is an illustration in plan view of a second embodiment of an apparatus according to the invention employing X-ray reflective diffraction.

Referring now to FIG. 2, there is shown in plan view an apparatus according to the invention employing X-ray reflective diffraction, the apparatus indicated by 300. The apparatus 300 comprises the lithography tool 20 incorporating wafer in cassettes 302 for supplying wafers to be processed in the tool 20 and wafer out cassettes 304 for receiving wafers which have been exposed in the tool 20. The apparatus 300 further comprises a diffraction tool 310 comprising first and second parts mounted on an arcuate support 312 attached to the lithography tool 20 via a gliding air bearing table indicated by 315. The first and second parts are mounted at a side of the lithography tool 20 substantially in a horizontal plane. Moreover, the arcuate support 312 is slidably mounted on the table 315 so that its distance from the wafer 190 can be varied as required for different wafer 190 compositions and dimensions and hence different Bragg diffraction angles.

The first part of the diffraction tool 310 comprises the point X-ray source 110, a 4-bounce monochromator 318 and a collection of horizontal slits 320 for generating an outgoing beam 325 of X-ray radiation propagating towards the wafer 190; the slits are adjustable to align the beam 325 to an edge of the wafer 190.

Adjustment of the slits is achieved by placing a powder specimen of an appropriate material where the beam 325 should impinge above the chuck 40, thereby enabling a range of reflected beams to be produced from the specimen which the second part of the diffraction tool can detect; the specimen can, for example, be a relatively small glass capillary tube comprising GaAs or InP powder.

The monochromator 318 and the slits 320 are mounted on an arm 330 which is pivotally mounted with respect to the source 110; such pivotal mounting enables the diffraction tool 310 to cope with different wafer compositions and wafer sizes. Moreover, the arm 330 and the source 110 are slidably mounted on the arcuate support 312 so that the angle (p can be varied depending upon wafer composition or source 110 target composition, namely X-ray radiation wavelength.

Likewise, the second part of the diffraction tool 310 includes a large area X-ray detector 340 slidably mounted on the arcuate support 312 so that its angle (p can also be adjusted depending upon wafer 190 composition and source 110 target composition. Large area in this context means a detector having an X-ray sensitive detecting area substantially in excess of 1 $cm^2$.

The diffraction tool 310 is operable such that the source 110 generates X-ray radiation at a wavelength of 0.154 nm from a copper target, the radiation propagating through the monochromator 318 and the slits 320 to form an X-ray beam 325 which propagates to an edge of the wafer 190 whereat it is diffractively reflected and a portion thereof propagates away from the wafer 190 to the wide area detector 340. In a similar manner to the apparatus 10 in FIG. 1, the detector 340 in FIG. 2 provides a maximum pulse rate at its output when crystal planes of the wafer 190 are correctly angularly aligned to the diffraction tool 310.

The apparatus 300 further comprises the alignment control unit 50, the lithography control unit 60, the chuck 40, the chuck actuator unit 45 and the mask actuator unit 65; these items are not shown in FIG. 2 but form part of the apparatus 300. A pulse output from the large area detector 340 is connected to the input $I_1$ of the alignment control unit 50 in a similar manner to the detector 160 in the apparatus 10. A radiation shield (not shown in FIG. 2) is located above the diffraction tool 310 to at least partially prevent stray X-ray radiation reaching the wafer 190 and human operators of the apparatus 300.

The parts of the diffraction tool 310 are arranged symmetrically about an axis F–F' as shown in FIG. 2. The axis F–F' passes through the centre of the wafer 190 and intersects a peripheral edge of the wafer 190 where the beam 325 impinges onto the edge. Optical axes of the parts of the tool 310 subtend the angle φ relative to the axis F–F' as shown.

If first order <220> diffractive reflectance is employed, the parts are adjusted on their arcuate support 312 such that the angle φ is in the order of 60°. If higher order diffractive reflectance is employed, for example <440> or <660> order, the angle φ can be decreased towards 0° thereby making the apparatus 300 more compact.

Tables 1 and 2 provides examples of angle 2θ (φ=90°−θ) for various source 110 target compositions, wafer compositions and diffraction orders. It can be seen from Tables 1 and 2 that some combinations of wafer composition, diffraction order and target composition do not provide workable angles with regard to diffraction tool 310 set-up. The first order <220> reflective diffraction mode always results in workable angles as provided in Table 1.

TABLE 1

Diffraction angle 2θ associated with <220> reflective diffraction order

| Wafer composition | Mo target composition | Cu target composition | Co target composition | Fe target composition |
|---|---|---|---|---|
| InP | 19.6° | 43.5° | 50.9° | 55.5° |
| GaAs | 20.4° | 45.3° | 53.2° | 58.0° |
| Ge | 20.2° | 45.3° | 53.1° | 57.9° |
| Si | 21.3° | 47.3° | 55.5° | 60.6° |

TABLE 2

Diffraction angle 2θ associated with <440> reflective diffraction order

| Wafer composition | Mo target composition | Cu target composition | Co target composition | Fe target composition |
|---|---|---|---|---|
| InP | 40.0° | 95.8° | 119.0° | 137.7° |
| GaAs | 41.6° | 100.8° | 127.0° | 151.2° |
| Ge | 41.5° | 100.7° | 126.9° | 150.9° |
| Si | 43.4° | 106.7° | 137.5° | >180° |

The apparatus 300 is initially calibrated in a similar manner to the apparatus 10 when the mask 35 in installed into the apparatus 300, namely the test wafer is first aligned to the diffraction tool 310 and the mask 35 is then aligned to the cleaved edge of the test wafer. The test wafer is then removed for production wafers, for example the wafer 190, to be loaded into the apparatus 300 and processed therein.

When processing the wafer 190 installed onto the chuck 40 of the apparatus 300, the alignment control unit 50 adjusts the angular orientation of the wafer 190 until a pulse rate from the detector 330 is maximum; this maximum corresponds to correct alignment. After registration of the mask 35 to the wafer 190 has been undertaken, the unit 60 then activates the source 25 to print the pattern on the mask 35 onto an organic resist layer coating an upper exposed major surface of the wafer 190.

The apparatus 300 provides a major benefit that a relatively larger proportion of radiation incident on the edge of the wafer 190 is reflected in the apparatus 300 compared to the proportion of radiation transmitted through the wafer 190 in the apparatus 10. At a radiation wavelength of 0.154 nm, the l/e attenuation depth for radiation propagation into the wafer 190 comprising gallium arsenide is only around 10 μm, e having a value of substantially 2.818. As a consequence, pulse count rates in the detector 330 can approach 10000/second which provides the control unit 50 with a relatively larger statistical sample for establishing a maximum value corresponding to best alignment. For a given X-ray source power, the apparatus 300 is thereby capable of aligning the wafer 190 to its diffraction tool 310 more accurately and rapidly than the apparatus 10 can to its diffraction tool 100. Moreover, the apparatus 300 does not expose an edge peripheral region of the wafer 190 as occurs during alignment in the apparatus 10; the edge peripheral region can be as much as 5 mm from an edge of the wafer 190.

Although the beam 325 only propagates a few μm into the wafer 190, the diffraction tool 310 is relatively insensitive to edge surface roughness of the wafer 190 provided that crystalline damage is not present as a consequence of the surface roughness.

Figure 3:
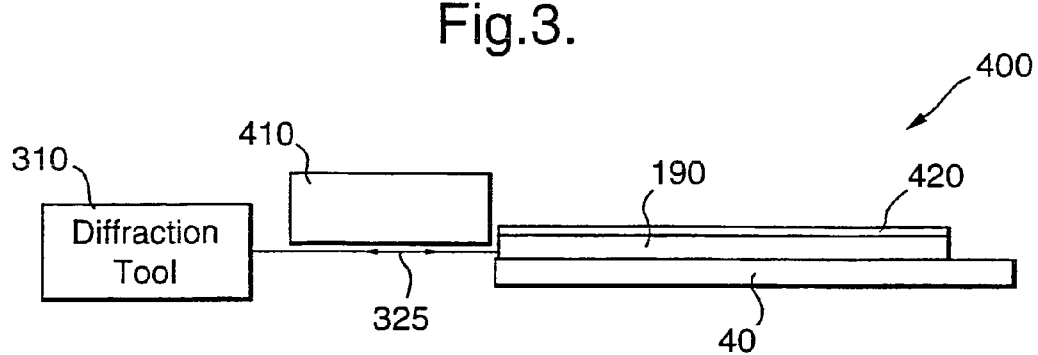
FIG. 3 is an illustration inside view of part of the second embodiment shown in FIG. 2.

Referring now to FIG. 3, there is shown a side elevation view of part of the apparatus 300 illustrated in FIG. 2; the view is indicated by 400. An X-ray radiation shield 410 is situated above the beam 325 providing operator protection and attenuating stray radiation which could cause unwanted exposure of an organic resist layer 420 on an upper exposed major surface of the wafer 190. As a consequence of the beam 325 impinging on an edge of the wafer 190 and being attenuated within μm of the edge surface, the beam 325 does not itself cause significant exposure of the resist layer 420 when the apparatus 300 is in operation.

Figure 4:
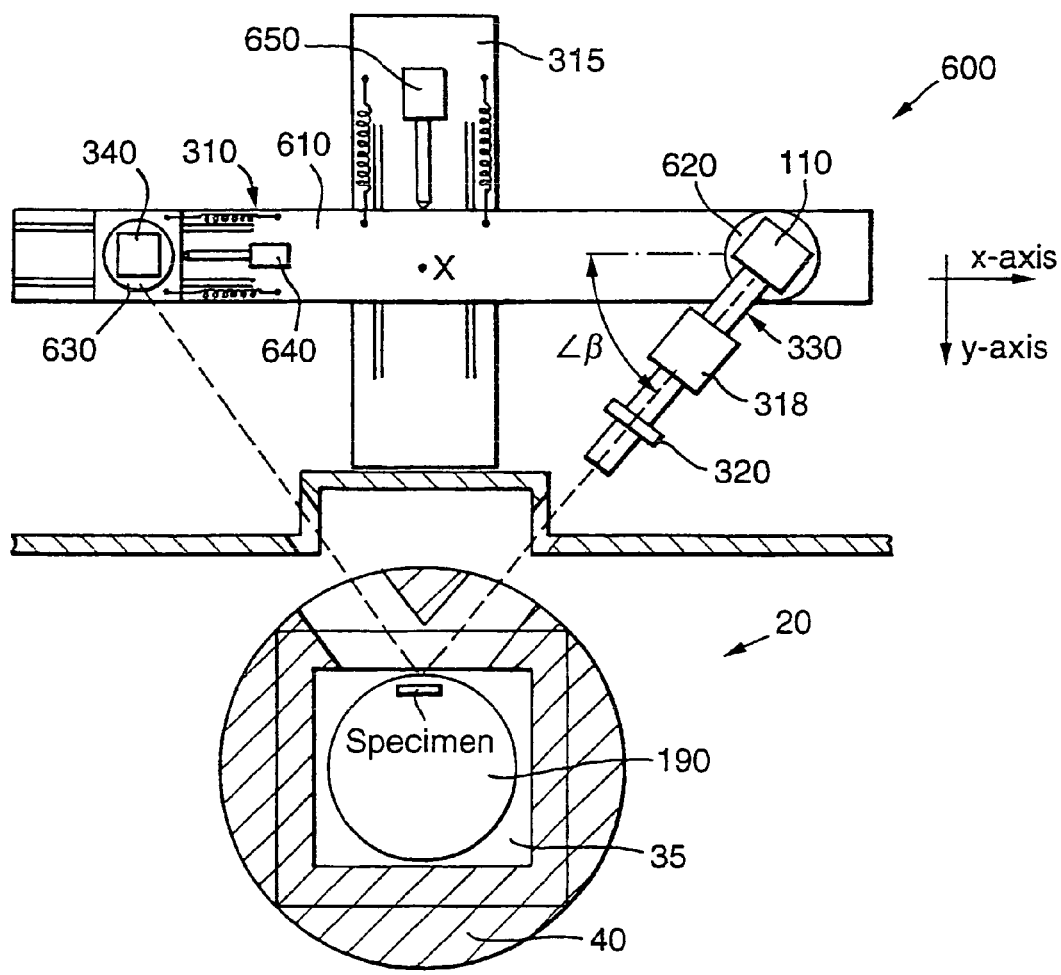
FIG. 4 is an illustration in plan view of a modified version of the second embodiment of the invention shown in FIGS. 2 and 3 incorporating a linear support member onto which its X-ray diffraction tool is adjustably mounted.

Referring now to FIG. 4, there is shown a modified form of the apparatus 300 indicated by 600. In a modified apparatus 600, the arcuate support 312 of the apparatus 300 is substituted with a straight linear support member 610 slidably mounted onto the table 315.

The detector 340 is slidably mounted on the member 610 and its position adjustable along an elongate axis of the member 610. The linear support member 610 is simpler and cheaper to implement than the corresponding arcuate support 312, thereby reducing cost of manufacturing the apparatus 600.

The diffraction tool 310 of the apparatus 600 is relatively complex to align and calibrate.

Adjustment of the monochromator 318 involves the steps of:

(a) rotating the arm 330 using a source goniometer 620 so that the arm 330 lies parallel to an elongate axis of the member 610;

(b) removing the slits from the collection of slits 320;

(c) rotating the detector 340 using its detector goniometer 630 so that its X-ray sensitive region faces towards the source 110;

(d) activating the source 110 to emit X-ray radiation and then aligning the monochromator 318 to give a maximum X-ray photon count rate at the detector 340; and (e) deactivating the source 110 and then replacing the slits in the collection 320.

Subsequent alignment of the tool 310 to the chuck 40 involves the steps of:

(a) rotating the arm 330 to subtend an angle β with the elongate axis of the member 620 where β=90°−$β_B$, $β_B$ being the Bragg angle for diffraction from {110} planes of an appropriate diffraction order, for example <440>; precise alignment is not necessary, for example an alignment error of +/−1° is usually sufficient;

(b) removing the slits from the collection 320;

(c) placing a relatively small polycrystalline specimen including randomly orientated crystalline planes onto the chuck 40, and then rotating the chuck 40 to bring the specimen to a position where X-ray radiation propagating from the source 110 through the monochromator 318 and the collection 320 impinges on the specimen;

(d) rotating the detector 340 on its goniometer 630 to face at its sensitive face towards the chuck 40;

(e) translating the detector 340 using an x-axis translation adjuster 640 along the elongate axis of the member 610 such that it lies at a similar distance from a central point X of the member 610, the point X being at an intersection of the elongate axis of the member 610 to an orthogonal axis running through a central point of the chuck 40 and perpendicular to the elongate axis;

(f) activating the source 110 to emit X-ray radiation;

(g) translating the member 610 using a y-axis adjuster 650 to generate a maximum X-ray count rate at the detector 340;

(h) adjusting a vertical z-axis adjuster on the goniometer 620 to further maximise the count rate from the detector 340;

(i) reinstalling the slits in the collection 320;

(j) adjusting vertical z-axis position elevation of the goniometer 630 to obtain to further maximise the count rate from the detector 340;

(k) deactivating the source 110 and removing the specimen from the chuck 40.

With regard to aligning the mask 35 to the diffraction tool 310 during initial calibration, the following method can be adopted, the method comprising the steps of:

(a) installing the mask 35 into the tool 20;

(b) placing the test wafer onto the chuck 40;

(c) activating the source 110;

(d) rotating the chuck 40 until a maximum X-ray count rate is provided from the detector 340;

(e) viewing the test wafer through the mask 35 using a split-screen binocular microscope and then rotating a holder onto which the mask 35 is mounted to align a pattern on the mask 35 with the cleaved edge of the test wafer; and (f) deactivating the source 110 and then removing the test wafer from the chuck to complete calibration.

If sufficiently reproducible registration of masks to the holder can be achieved, registration of the mask 35 to production wafers on the chuck 40 in the lithographic tool prior to pattern transfer during irradiation from the source 25 is not required.

It will be appreciated that modifications can be made to the apparatus 10, 300, 600 without departing from the scope of the invention. For example, in the apparatus 10, the orientation of crystallographic planes of the wafer 190 can be accurately determined by measuring positions of several diffracted beams and then calculating a line of intersection for the beams. After having thereby determined the wafer 190 orientation, the wafer 190 can be rotated by a known amount to angularly align it with the mask 35. This approach has a disadvantage of requiring more computation than required in the aforementioned apparatus 10 shown in FIG. 1.

If necessary, the apparatus 10, 300, 600 can be enclosed entirely in an overall X-ray shield to protect associated human operators of the apparatus 10, 300, 600.

The diffraction tools 100, 310 can have their respective parts mounted on actuators, for example on stepper motors actuators, which are controllable from the wafer alignment control unit 50 so that the apparatus 10, 310 can be automatically switched from coping with one type of wafer to another.

The apparatus 10, 300 can, if necessary, be operated at wavelengths other than X-ray wavelengths provided that Bragg diffraction occurs enabling crystallographic orientation of the wafer 190 to be determined. X-ray radiation is defined here as having a wavelength in a range of 0.01 nm to 10 nm.

What is claimed is:

1. A method of aligning a substrate in an apparatus, characterised in that the apparatus incorporates a lithographic tool for printing a pattern onto the substrate and a diffractive substrate angle measuring tool for measuring angular orientation of one or more crystal planes of the substrate, the method comprising:

(a) calibrating angular orientation of the pattern relative to the measuring tool;

(b) inserting the substrate into the lithographic tool; and (c) measuring angular orientation of said one or more crystal planes of the substrate using the measuring tool, and rotating the substrate until its one or more crystal planes angularly align to the pattern;

the pattern thereby angularly aligned to the substrate and to said one or more crystal planes thereof, wherein the measuring tool operates at X-ray radiation wavelengths and measures diffracted X-ray radiation resulting from Bragg diffraction within the substrate, the correct angular orientation of said one or more crystal planes being determined by an X-ray count rate in an X-ray detector of said measuring tool.

2. A method according to claim 1, wherein correct angular orientation of said one or more crystal planes is determined by finding an orientation of the substrate relative to the measuring tool resulting in a maximum X-ray count rate in an X-ray detector of said measuring tool.

3. A method according to claim 1, wherein a diffracted X-ray beam is generated for measuring angular orientation of said one or more crystal planes by transmitting an interrogating X-ray beam through the substrate.

4. A method according to claim 1, wherein a diffracted X-ray beam is generated for measuring angular orientation of said one or more crystal planes by reflecting an interrogating X-ray beam from the substrate.

5. A method according to claim 4, wherein the interrogating beam impinges onto a peripheral edge of the substrate.

6. A method according to claim 1, wherein the measuring tool uses first, second or third order diffraction modes to measure angular orientation of said one or more crystal planes.

7. A method according to claim 1, wherein the substrate is a single crystal wafer.

8. A method according to claim 1, wherein the lithographic tool comprises a mask proximity printer, a step-and-repeat lithographic camera, or an electron beam lithography system using deflected electron beams to print the pattern onto the substrate.

9. A method according to claim 1, wherein in step (a), calibration includes the steps of:

(a) inserting a test substrate into the lithographic tool, the test substrate being cleaved to expose a cleaved edge corresponding to a crystal plane;

(b) angularly aligning the test wafer to the measuring tool to yield a maximum radiation count rate from its detector; and (c) angularly aligning features of the pattern relative to the cleaved edge.

10. A method according to claim 1, wherein the pattern is included on a lithographic mask loadable into the lithographic tool.

11. A method according to claim 1, wherein the measuring tool is disposed into two parts, said parts adjustably mounted to enable different diffraction angles to be selected when using the method.

12. A method according to claim 1, wherein printing the pattern onto the substrate comprises exposing a resist layer of the substrate.

13. An apparatus for use in aligning a substrate, the apparatus comprising:
- a lithographic tool for printing a pattern onto the substrate; and
- a diffractive substrate angle measuring tool for measuring angular orientation of one or more crystal planes of the substrate, the apparatus operable to angularly align said one or more crystal planes to the pattern and then print the pattern onto the substrate, wherein the measuring tool includes an X-ray source and an X-ray detector, the X-ray source arranged to generate a beam for interrogating the substrate and the X-ray detector arranged to receive diffracted radiation resulting from Bragg diffraction of the beam, the correct angular orientation of said one or more crystal planes being determined by an X-ray count rate in the X-ray detector.

14. An apparatus according to claim 13, wherein the measuring tool is disposed to detect radiation transmitted and diffracted through the substrate.

15. An apparatus according to claim 13, wherein the measuring tool is disposed to detect radiation reflected and diffracted from the substrate.

16. An apparatus according to claim 15, wherein the measuring tool incorporates a large area X-ray detector for detecting diffracted radiation reflected from the substrate.

17. An apparatus according to claim 13, wherein the X-ray source includes an X-ray target for generating radiation for the beam, the target being of a material including copper, cobalt, iron, silver or molybdenum.

18. An apparatus according to claim 13, wherein the measuring tool is disposed in two parts adjustably mounted with respect to the lithographic tool, thereby enabling adjustment of the measuring tool to cater for a range of Bragg diffraction angles associated with radiation diffracted from the substrate.

19. An apparatus according to claim 18, wherein the two parts of the measuring tool are adjustably mounted on an arcuate support member connected to the lithography tool.

20. An apparatus according to claim 18, wherein the two parts of the measuring tool are adjustably mounted on a substantially linear support member connected to the lithography tool.

21. An apparatus according to claim 18, wherein the measuring tool is operable to function in first, second or third order diffraction modes.

22. An apparatus according to claims 13, wherein the measuring tool is to determine an X-ray count rate.

23. An apparatus according to claims 13, wherein the substrate is devoid of an orientational flat formed therein.

* * * * *